United States Patent [19]
La Haye et al.

[11] Patent Number: 5,105,993
[45] Date of Patent: Apr. 21, 1992

[54] DISPOSABLE MEDICAL DISPENSER WITH A FILTERING DISPENSER NOZZLE

[75] Inventors: Peter G. La Haye, Medina, Wash.; Peter W. Chan, Northridge, Calif.

[73] Assignee: La Haye Laboratories, Inc., Redmond, Wash.

[21] Appl. No.: 458,891

[22] Filed: Dec. 29, 1989

[51] Int. Cl.⁵ ............................................. B67D 5/58
[52] U.S. Cl. .................... 222/189; 222/420; 210/321.89
[58] Field of Search .............. 604/126, 295, 296, 299; 210/251, 321.78, 321.79, 321.8, 321.87, 321.88, 321.89, 500.23; 222/189, 212, 206, 215, 420, 562

[56] References Cited

U.S. PATENT DOCUMENTS

| | | | |
|---|---|---|---|
| 920,791 | 5/1909 | Tonini | 215/308 |
| 3,592,245 | 7/1971 | Schneller | 141/25 |
| 3,722,694 | 3/1973 | Agranat | 210/321 |
| 3,760,949 | 9/1973 | Carey et al. | 210/321.8 |
| 3,951,798 | 4/1976 | Haldopoulos | 210/452 |
| 3,954,623 | 5/1976 | Hammer | 210/436 |
| 4,136,036 | 1/1979 | Columbus | 210/516 |
| 4,190,542 | 2/1980 | Hodgson | 210/282 |
| 4,234,095 | 11/1980 | Safianoff | 215/232 |
| 4,329,229 | 5/1982 | Bodnar et al. | 210/321.89 |
| 4,435,289 | 3/1984 | Breslau | 210/637 |
| 4,463,880 | 8/1984 | Kramer et al. | 222/189 |
| 4,664,800 | 5/1987 | Raines | 210/445 |
| 4,879,032 | 11/1989 | Zemlin | 210/321.89 |
| 4,917,271 | 4/1990 | Kanner et al. | 222/189 |
| 4,930,667 | 6/1990 | Holzner, Sr. | 222/189 |
| 4,938,389 | 7/1990 | Rossi et al. | 222/189 |

FOREIGN PATENT DOCUMENTS

| | | | |
|---|---|---|---|
| 3628197 | 2/1988 | Fed. Rep. of Germany | 222/420 |
| 9194751 | 11/1984 | Japan | 222/420 |

*Primary Examiner*—Michael S. Huppert
*Assistant Examiner*—Gregory L. Huson
*Attorney, Agent, or Firm*—Gordon W. Hueschen

[57] ABSTRACT

There is disclosed a dispensing container for dispensing sterile liquid medicament, for example into the eyes, e.g., liquid artificial tears, in which a filter is provided in the dispensing nozzle or in a closure member for the container having pores which are sufficiently small to filter out microorganisms, whereby an antibacterial agent need not be included in the medicament. A cap is provided for the dispensing nozzle, which cap may have an absorbent pad impregnated with an antibacterial agent to maintain the exit port of the dispensing nozzle sterile. The container may also have a filter provided in a vent in a wall thereof, whereby air drawn into the container to replace liquid medicament ejected through the nozzle thereof will be sterilized. The filter preferably comprises a plurality of hollow elongated filter fibers or tubes bent back on themselves and secured in the nozzle or closure member by a suitable potting material, having in any case pores not larger than about 0.2 micron in diameter.

11 Claims, 2 Drawing Sheets

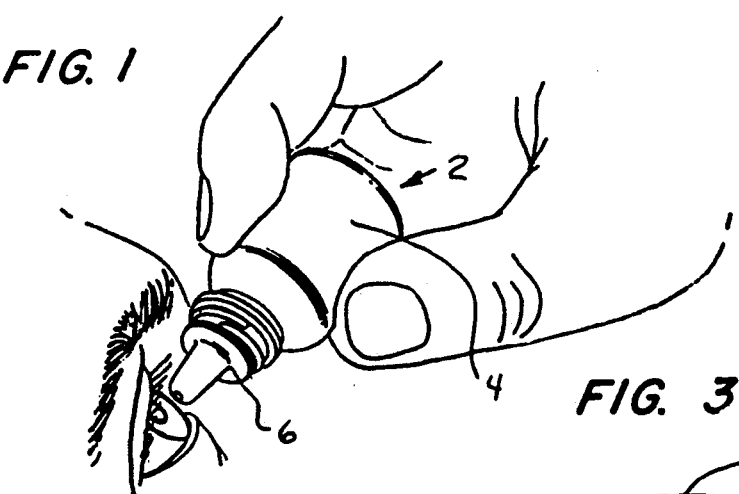
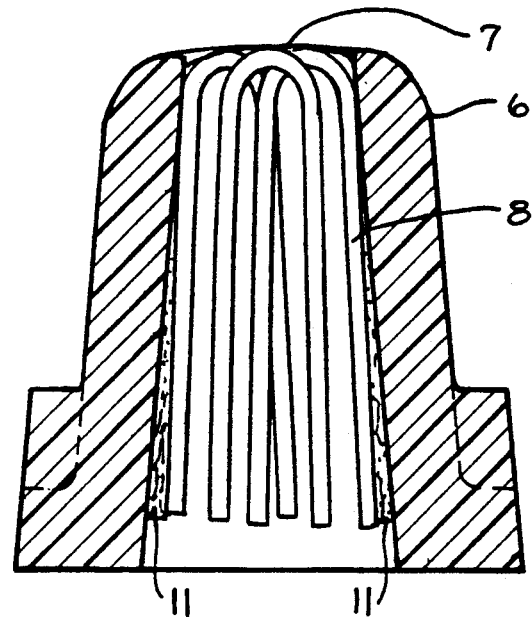
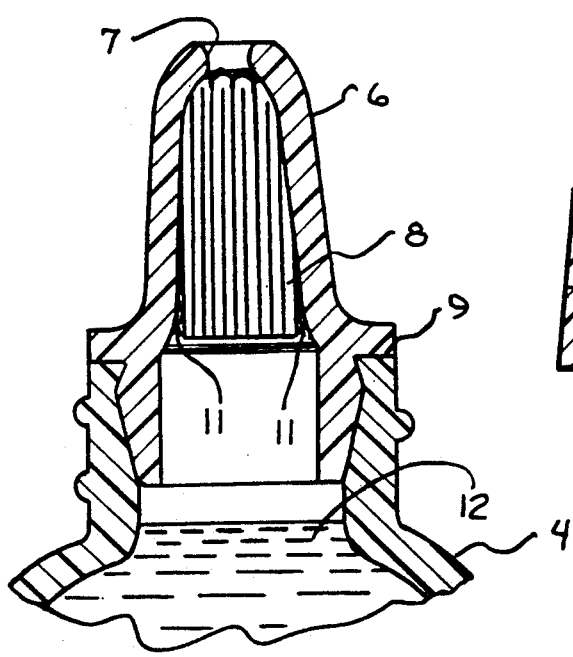
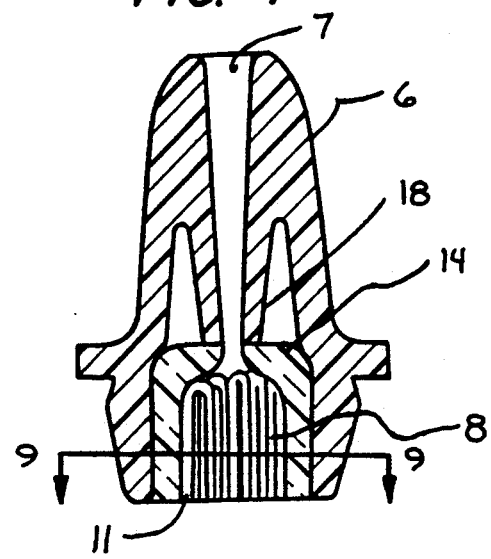
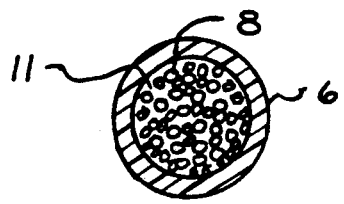

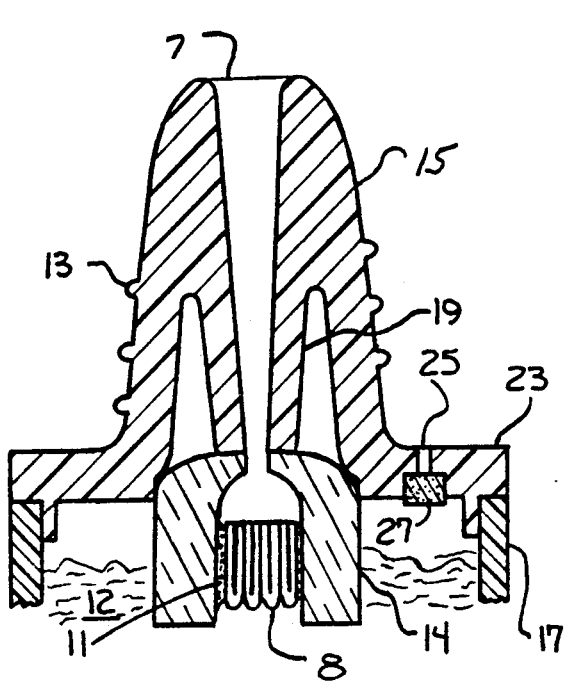
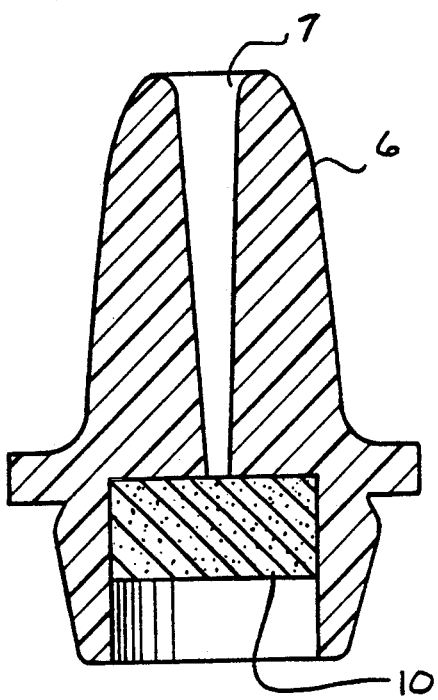
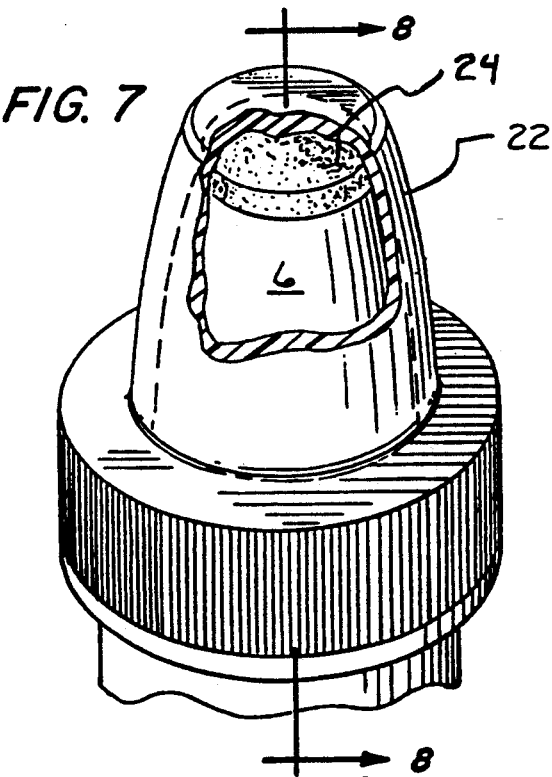
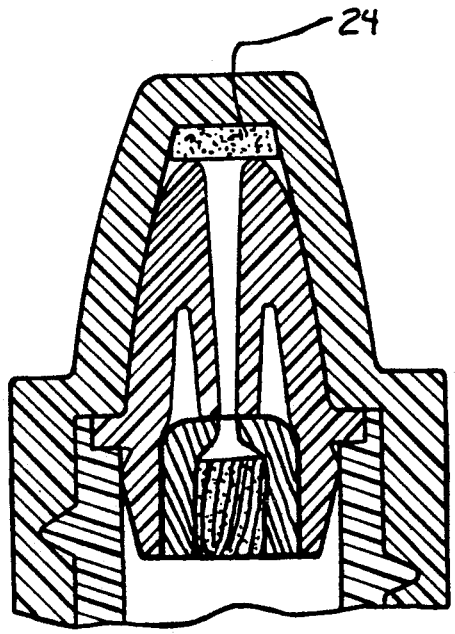

DISPOSABLE MEDICAL DISPENSER WITH A FILTERING DISPENSER NOZZLE

BACKGROUND OF THE INVENTION

1. Field of the Invention

The present invention relates to a disposable container for dispensing a liquid medication or medicament and, more particularly, to a relatively inexpensive disposable container with or without liquid medication, e.g., liquid artificial tears, contained therein, which can maintain the sterility of a sterile liquid medication contained therein without the necessity of a preservative being present in said liquid medication, either prior to packaging or subsequently.

2. Description of Related Art

Patient medications are frequently prescribed which are to be dispensed in a metered amount over a predetermined time period. Thus, the medication is prepared and marketed in a predetermined quantity adapted for a predetermined number of individual self-administerable dosages, and the patient usually self-administers the medication over a period of days. A common utilization of such dispensers is in the field of ophthalmology, wherein various forms of medication are frequently prescribed for the patient to be dispensed in metered drops from a disposable container. Examples of such medication can be decongestants, antibiotics, anti-inflammatories, antiglaucoma medication, antibacterials, anesthetics, mydriatics, anticholinergics, and miotics, as well as combinations thereof. Frequently such medication requires the addition of an antibacterial agent such as benzalkonium chloride, thimerosal, chlorobutanol, zepazonium, other quaternary ammonium compound, or other bacteriostatic or bactericidal agent. Such agents are frequently necessary to preserve the sterility of the medication during the period in which it is stored in the dispensing container. However, such antibacterial agents also frequently contribute to, or are solely responsible for, the stinging effect perceived by a patient when self-administering the drops. Thus, the actual prescribed therapeutic medication may not itself create an unpleasant sensation in the eye of a user, but the preservative therein will frequently contribute to or independently cause such effect.

Numerous examples of attempts to maintain the sterility of either a liquid to be dispensed or a liquid to be collected are of record in the medical field. For example, U.S. Pat. No. 4,664,800 discloses a filter device for use with intravenous drip chambers.

U.S. Patent 3,951,798 discloses a dispenser device provided with a filter member capable of separating fibrin and particulate material from blood serum, and for dispensing small amounts of the filtered serum. The filter is temporarily retained within the cap. After the fluid to be filtered and dispensed is placed within the container, the cap and filter assembly is screwed over the mouth of the container, which forces the filter into place. Subsequently, the filter maintains the particulate material within the dispensing bottle.

U.S. Pat. No. 3,592,245 discloses a dispensing package for medicaments which are to be dissolved in a parenteral solution container prior to use. A membrane filter is disposed between the container and the cap and serves the purpose of removing particulate material which may have solidified from the solution during the shelflife of the product.

The following patents are cited of general interest as disclosing various forms of filtration systems, alone or in combination with storage containers: U.S. Pat. Nos. 920,791, 3,722,694, 3,954,623, 4,136,036, 4,190,542, 4,234,095, and 4,435,289.

Microgon, Inc. of Laguna Hills, Calif., has marketed a series of filter products which incorporate hollow tubular filter membranes or members in modules for small volume sterile filtration purposes, and for syringe filters, to accommodate the aspiration or injection of fluids into vials, ampules, test tubes, and other vessels.

The prior art is still seeking a relatively inexpensive disposable fluid medication container which can maintain a sterile environment for liquid medication contained or to be contained therein without the necessity of added preservative.

OBJECTS OF THE INVENTION

It is an object of the present invention to provide a novel dispensing container for dispensing sterile liquid medicament, particularly an ophthalmic medicament, and especially liquid artificial tears, in which a filter is provided in a dispensing nozzle, especially at the extreme outer end thereof at the end of an exit opening in the said nozzle, or elsewhere in the container, as for example in a closure member thereof, which filter has pores sufficiently small to block out microorganisms whereby antimicrobial agent need not be included in the sterile liquid medicament, and a combination thereof with a sterile liquid medicament itself, especially liquid tears. Other more specific objects of the invention will become apparent from the description which follows, and still others will be obvious to one skilled in the art.

The invention, then, inter alia, comprises the following aspects, singly or in combination:

An improved patient-dispensing container for releasing controlled amounts of a sterile liquid medicament contained therein while maintaining a sterile environment within the container, comprising:

a container housing member for storing liquid medicament, the interior of which is in communication with a dispenser nozzle member having an outlet port, and filter means mounted within the housing member or dispenser nozzle member between the stored liquid medicament and the outlet port, said filter means including a series of hollow tubular filters providing egress openings or pores of not greater than approximately 0.2 micron in diameter, and means for transmitting the liquid medicament into the interior of the hollow tubular filters to cause egress thereof through the said egress openings or pores and out of said outlet port, whereby the sterile liquid medicament can be dispensed from said container while retaining sterility of the sterile liquid medicament remaining therein, thereby enabling the storage of a sterile liquid medicament in said container and dispensation of sterile liquid medicament from said container without the necessity of providing antibacterial or other preservative in said liquid medicament; such a dispensing container wherein the housing member includes a closure member which is secured to the dispenser nozzle member with a sterile liquid-tight connection and wherein filter means are mounted in said closure member; such a dispensing container wherein filter means are provided in the dispenser nozzle member and the dispenser nozzle member is secured to the housing member with a sterile liquid-tight connection; such a dispensing container wherein the hollow tubular filters are hydrophilic; such a dispensing container wherein the tubular filters are a combination of cellulose nitrate, cellulose acetate, and glycerine; such a dispensing container wherein the hollow tubular filters are bent with their respective end openings aligned in the same direction; and such a dispensing container further including a releasably securable closure cap means having means for retaining an antibacterial agent in contact with the exterior surface of the dispenser nozzle member when said cap means is in place on said nozzle member.

Further, a combination of liquid medicament, free of preservative agent, and a sterile dispensing container which retains a sterile environment for the liquid medication therein during storage and dispensing, comprising:

a container housing member for storing the liquid medication, a dispenser nozzle member, having an outlet port, connected to the housing member with a sterile liquid-tight connection, a predetermined quantity of sterile liquid medicament comprising therapeutic ingredient and carrier fluid with no added preservative agent in said container housing member, filter means mounted within the dispenser nozzle member comprising bent hollow tubular filter members having egress openings or pores of a size to prevent passage of bacteria, the respective openings of the ends of the tubular filter members being positioned adjacent each other, and means sealing the filter means inside said dispenser nozzle member to require the liquid medicament to pass only through the filter means during dispensing of the liquid medicament; such a combination further including sterile filter means mounted in a vent in the container to assist transmission of air into the housing member; such a combination further including releasably securable closure cap means including means for sterilizing the exterior surface of the outlet port of the dispenser nozzle member when said cap means is in place on said nozzle member; and such a combination wherein the sterilizing means includes a sterilizing material which contacts the exterior surface of the outlet port when said cap means is secured to the nozzle member.

Moreover, an improved patient-dispensing container for releasing controlled amounts of a sterile liquid medicament contained therein while maintaining a sterile environment within the container, comprising:

a flexible housing member having a closure member for storing the liquid medicament and comprising a dispenser nozzle member with an outlet port;

filter means mounted within the closure member or the dispenser nozzle member between the stored liquid medicament and the outlet port, and means for rigidly securing the filter means within the dispenser nozzle member or closure member to provide a sterile liquid-tight connection therebetween, the filter means including a series of hollow tubular filter members providing egress openings or pores of not more than approximately 0.2 micron in diameter, whereby sterile liquid medicament can be dispensed through the egress openings or pores while retaining the sterility of the contents of the container to enable the use of liquid medicament without the necessity of the presence of an antibacterial preservative therein; such a dispensing container wherein the hollow tubular filter members are bent with their respective end openings positioned in the same direction and the means for rigidly securing the filter means to the nozzle member or closure member includes a potting material; such a dispensing container further including sterile filter means located in a vent in the container to assist transmission of sterile air into the housing member; such a dispensing container further including releasably securable closure cap means including means for periodically sterilizing the exterior surface of the outlet port of the dispenser nozzle member; and such a dispensing container wherein the sterilizing means includes a sterilizing material which contacts the exterior surface of the nozzle member at the outlet port thereof when said cap is secured to the nozzle member.

Additionally, a combination of liquid medication, free of preservative agent, and a disposable sterile dispensing container which retains a sterile environment for the liquid medication during storage and dispensing, comprising:

a liquid-tight housing member for storing the liquid medication, a dispenser nozzle member having an outlet port connected to said housing member with a sterile liquid-tight connection, a predetermined quantity of sterile liquid medication comprising therapeutic ingredient and carrier fluid without added preservative agent in said housing member, filter means securely mounted within the dispenser nozzle member and having egress openings or pores of a size to prevent passage of bacteria therethrough, and means sealing the filter means in said nozzle member to permit the liquid medication to pass only through the filter means during dispensing of the sterile liquid medication in said housing member; such a combination further including a sterile filter means mounted in a vent in said container to assist transmission of sterile air into the housing member; such a combination wherein the filter means comprises a series of bent tubular hydrophilic filter members comprising a combination of cellulose nitrate, cellulose acetate, and glycerine; such a combination wherein the filter means comprises a ceramic porous block having egress openings or pores no greater than about 0.2 micron in diameter; such a combination further including releasably securable closure cap means having means for retaining an antibacterial agent in contact with the exterior of the dispenser nozzle member when in place thereon; such a combination wherein the dispenser nozzle member and the filter means are provided as an integral unit with the filter means sealed in the outlet port thereof at the outer end thereof; such a combination further including releasably securable means for periodically sterilizing the exterior surface of the outlet port of the dispenser nozzle member; and such a combination wherein the means includes releasably securable closure cap means comprising a sterilizing material which contacts the exterior surface of the nozzle member at the outlet port thereof when secured to the nozzle member.

Also, such a device wherein the filter means is located at the extreme outer end of the nozzle member in the exit port thereof; and such a combination wherein the filter means is located at the extreme outer end of the nozzle member in the exit port thereof.

Finally, such a combination wherein the contained medicament is liquid artificial tears.

THE INVENTION IN GENERAL

The present invention provides a combination of a liquid medication, free of added preservatives or preservative agents, and a dispensing container which is capable of maintaining a sterile environment for the liquid medication until the expiration date for usage of the medication, as well as the container alone as an independent contribution to the art, comprising all of the elements hereinafter described. A flexible housing member stores the liquid medication and can comprise a conventional plastic opaque or transparent bottle member, e.g., a squeeze bottle member. A relatively-rigid dispenser nozzle with an exit or outlet port for metering dispensation of the liquid medication is attached to the housing member, with a sterile liquid-tight connection, or even integral therewith. A filter assembly is mounted within the dispenser nozzle or in a closure member for the housing and preferably comprises a series of bent, hollow tubular filter members or a ceramic or glass filter block, either of which provide effective egress openings or pores of a size to prevent the passage of bacteria. The filter is sealed within the dispensing nozzle or closure member for the housing, and conveniently provides an integral unit for mounting to, or even as a part of, the housing member. A sterile venting port can also be provided in the nozzle or in the housing member itself to assist transmission of sterile air into the housing member to replace the volume of liquid material which is displaced and dispensed.

Finally, a closure cap can be provided, the dimensions of the cap and the dispenser nozzle being such as to ensure that a further element, namely a pad containing antibacterial agent, is pressed against the exterior end surfaces of the nozzle member adjacent the outlet or exit port thereof during storage.

As already stated, further aspects, objects and advantages of the present invention will be apparent to one skilled in the art and additional objects and advantages will become more fully apparent hereinafter from the following description and the annexed drawings which illustrate the preferred embodiments.

BRIEF DESCRIPTION OF THE DRAWINGS

FIG. 1 is a perspective view of an ophthalmic dispenser;

FIG. 2 is a cross-sectional view of the nozzle assembly and upper neck of the bottle;

FIG. 3 is an enlarged cross-sectional view of the hollow tubular filter and potting material in a preferred embodiment of the invention;

FIG. 4 is a cross-sectional view of an alternative embodiment of the nozzle assembly including a closure member;

FIG. 5 is a cross-sectional view of another alternative nozzle and closure member assembly;

FIG. 6 is a cross-sectional view of a further alternative embodiment of the nozzle assembly;

FIG. 7 is a partial perspective view with a cut-away portion showing a sterile closure cap;

FIG. 8 is a cross-sectional view of the embodiment of FIG. 7, and

FIG. 9 is a cross-sectional view of the embodiment of FIG. 4.

DETAILED DESCRIPTION OF THE PREFERRED EMBODIMENTS

The following description is provided to enable a person skilled in the medical dispensing field to make and use the present invention and sets forth the best modes contemplated by the inventors of carrying out their invention, but is not to be construed as limiting. Various modifications will be readily apparent to one skilled in this art, since the generic principles of the present invention have been disclosed herein specifically to provide an improved economical, disposable, sterile dispenser for liquid medication and the physical embodiments thereof have been described in detail.

Referring now to FIG. 1, a sterile liquid medication dispensing container of the type particularly useful in the field of ophthalmology is disclosed for dispensing metered drops of liquid medication 12 into the eye of a patient. The dispensing container 2 includes a bottle housing member 4 and a dispensing nozzle member 6. The housing member 4 is preferably formed of a molded flexible plastic resin. Preferably, the bottle housing 4 is designed to permit squeezing by the hand of the patient in order to facilitate the dispensing of the liquid medication contained therein. According to the present invention, such flexible housing advantageously provides means for forcing the liquid medicament into and through the pores of the filter member or members and out of the dispensing nozzle member 6 through the exit port thereof. A clear thermoplastic material such as a polyethylene resin can be used for the formation of the housing 4. Such bottles are well known to one skilled in this field.

The dispensing nozzle 6 includes an outlet port 7 of predetermined dimension to assist in the metered dispensing of drops into, for example, the eye of a patient, as shown in FIG. 1.

In a preferred embodiment of the present invention, the dispensing nozzle 6 is relatively rigid compared to the bottle housing 4 and is permanently adhered to the bottle housing 4 with a sterile, liquid-tight connection 9, which can be readily accomplished using an approved medical adhesive.

The liquid medication 12, illustratively liquid artificial tears, contained within the bottle housing 4 advantageously comprises only the necessary or essential therapeutic ingredients in a sterile solution or suspension form, e.g., sterile physiologically-acceptable saline solution, such as readily attained using an inert carrier fluid, e.g., sterile water, in which the essential therapeutic ingredient or ingredients are, e.g., suspended or dissolved to achieve the desired therapeutic purposes of the medication. Preservative compound or material, such as an antimicrobial preservative which has been traditionally utilized, is not required or employed. Thus, standard antibacterial agents such as benzalkonium chloride, thimerosal, chlorobutanol, zepazonium, or other quaternary ammonium compound, or other bacteriostatic or bactericidal agent, is no longer necessary. Typical examples of medicaments utilized in the ophthalmic field are artificial tears, decongestants, antibiotics, antiinflammatories, antiglaucoma agents, antibacterials, anesthetics, mydriatics, anticholingerics, miotics, and combinations thereof.

The present invention encompasses the provision of a relatively inexpensive mechanical filtration system to enable a throwaway or disposable container for the liquid medication. Thus, while literally millions of disposable medical patient-utilizable containers have been provided in both plastic and glass configurations, the present invention is uniquely directed in one embodiment to a combination comprising a liquid medicament without added antibacterial or other preservative and a dispensing container, which combination can be supplied to the patient to relieve the discomfort, irritation, and inconvenience resulting from side effects stemming from employment of a preservative. The dispensing container of the present invention maintains the necessary sterility within the economic considerations and limitations of a single usage or multiple usage disposable dispenser. These advantages are realized through the utilization of a relatively inexpensive filter member 8 which can be integrally formed in combination with the dispenser nozzle 6 or a filter-containment member such as 14 connected to nozzle 6.

Examples of such filters are the hollow tubular filter fiber members 8 disclosed, for example, in FIGS. 2 and 3. These tubular filter members 8 are of a membrane construction comprising a porous matrix having pores or egress openings sufficiently small to prevent the passage of microorganisms, thereby to maintain the sterility of the contents of the bottle housing member 4. The membrane filter can illustratively comprise fibers of a cellulose ester such as cellulose acetate, cellulose triacetate, cellulose nitrate, or other packed fibers such as polyethylene, nylon, Teflon TM polyvinyl chloride, polypropylene, epoxy glass, or the like. Advantageously, the hollow filter fiber has a pore size of approximately 0.2 micron or less. Hollow tubular filters sold by Microgon, Inc. of Laguna Hills, Calif., which comprise and are formed from a combination of cellulose nitrate, cellulose acetate, and glycerine, are examples of especially appropriate filter materials. Such materials provide an approximately 0.2 micron filter opening or pore size, with a filtration area of approximately 2 to 6 $cm^2$, depending upon the number of tubular filter fiber members utilized per unit area.

The tubular filter members 8 are hydrophilic and are advantageously potted with a urethane or other suitable adhesive or potting material 11 directly in the dispenser nozzle member 6 (see FIGS. 2 and 3) or in filter-containment member (e.g., 14 in FIG. 4 or 5) where the filter is located upstream from the outlet port of the nozzle member. The potting material 11 is employed to fix the filter members wherever they are located within nozzle 6 or within filter-containment member 14 and in general must be upstream from the outlet port 7 of the dispenser nozzle member 6 (see FIGS. 2, 3, 4, 5, and 9), thereby providing a rigid structure to ensure a controlled metered and filtered outlet opening.

Advantageously the filter means is located in the nozzle member sufficiently close to the exit port thereof to enable a drop of the medicament fluid, e.g., liquid artificial tears, coming through the filter means to drop directly into the eye or other desired location of the body without contacting a wall or surface of any other member or portion of the device. For this reason, location of the filter means at the extreme outer end of the nozzle member, in the exit port thereof, as shown in FIGS. 2 and 3, is highly desirable.

Advantageously, the hollow tubular filter members 8 are bent so that their open ends are positioned immediately adjacent each other pointing in the same direction toward the exterior outlet port 7 of the dispenser nozzle member 6, as shown in FIG. 5, or in the opposite direction as shown in FIGS. 2, 3 and 4. In FIG. 2, the tubular filter members 8 are potted directly in the nozzle member 6 in like manner as shown at 11 in FIG. 5 in order to both restrict the conduit and to provide potting material 11 for securement directly to the interior walls of nozzle member 6.

Alternative filters can be utilized, such as sintered glass or sintered ceramic blocks 10, which likewise can provide pore sizes of 0.2 micron or smaller to ensure the exclusion and blocking out of microorganism by preventing transmission therethrough, thereby to maintain the sterility of the liquid medication 12, e.g., liquid artificial tears, which is in this case totally free of any preservative agent, e.g., liquid tears in such sterile and preservative-free condition. A sintered glass filter block 10 is disclosed in FIG. 6 as an alternative filter embodiment which can be employed according to the present invention.

Another alternative embodiment is shown in FIG. 4, wherein the specific filter-containment member 14 contains either a sintered glass or ceramic filter member (see 10 in FIG. 6) or, as shown in FIG. 4, tubular filter members 8. The member 14 can be formed, for example, of a polyurethane material or of the same material of which bottle housing member 4 is formed. A tubular alignment or support column 18 can be included to assist in the mounting of housing closure member 14 within dispenser nozzle 6.

As can readily be seen in FIG. 5, the upper neck of the nozzle portion 15 of a bottle housing 17 can comprise appropriate ribs or threads 13 for permitting the attachment by screwing on of a closure cap (not shown) in conventional manner. Additionally, the dispenser nozzle member 15 can be permanently adhered or otherwise secured to the bottle housing 17, thus further ensuring that liquid medication 12 therein, e.g., liquid artificial tears, will maintain its sterility without added preservative.

Dispensing nozzle member 15 can be formed as an integral unit with or for mounting on bottle housing 17. The nozzle member 15 advantageously can include a column support member 19 extending, inwardly from the outlet port 7. Interior filter-containment member 14 can be in the form of a hollow ported plastic block having tubular filter members 8 bent into individual generally U-shapes and potted therein with potting material 11 to seal the interior of the plastic block. Liquid medication 12 contained therein must pass through the side walls of the tubular filter members 8 and continue through the hollow tubular members in the potted section in order to egress through the central opening provided by column support member 19 to the outlet port 7. The bottom of the column support member 19 as well as any abutting portion of nozzle member 15 sidewalls or bottom walls and the top of member 14 are adhered together in a sterile, liquid-tight connection, with or without suitable adhesive (not shown).

Dispensing nozzle 15 has a lower base member 23 which is ported or vented at one side with a passageway 25. The interior end of passageway 25 is provided with an enlarged shoulder for receiving a filter member, for example and as shown, a sintered glass filter member 27. This passageway 25 provides a sterile venting port to the interior of the bottle housing 17. As will be readily understood, the sterile filter block or pad 27, which is permanently adhered or press fit into base member 23 to block conduit or passageway 25, likewise provides a pore size of 0.2 micron or less to preclude transmission of microorganisms and maintain sterile conditions inside bottle housing 17.

Referring now to FIG. 7, a closure cap 22, representatively of rigid polyethylene, is there shown as supporting a storage pad 24 for retention of an antibacterial agent and to be located in contact with the exterior surface of the dispenser nozzle 6 adjacent exit port 7. Thus, as shown in FIG. 8, each time the closure cap 22 is threaded onto or otherwise secured (as by a snap fit) to nozzle 6 or 15 of housing 4 or 17, the exterior surfaces of the dispensing nozzle outlet port 7 are maintained in sterile condition by contact with antibacterial pad 24 which may, for example, be formed of a gauze or lint-free absorbent material containing usual antibacterial agents such as benzalkonium chloride, thimerosal, chlorobutanol, zepazonium, other quaternary ammonium compound, or other bacteriostatic or bactericidal agent.

As can be readily appreciated, the dispensing container 2 comprising flexible housing member 4 can be readily, conveniently, and conventionally utilized by a patient for dispensing metered quantities of liquid medication, for example, into the eye. The dispenser nozzle member 6 is relatively rigid to ensure that an appropriate number of metered and filtered drops are provided through the outlet port 7 of the dispenser nozzle member 6. The filter means comprising filter members 8 is integrally mounted within the dispenser nozzle member 6 and can comprise either the series of hollow bent tubular filters 8 or, alternatively, a sintered filtered block 10, in either case to provide egress openings or pores of approximately 0.2 micron or less in diameter, whereby the liquid medication 12 can be dispensed through nozzle member 6 and exit port 7 via the upstream egress openings or pores while retaining and maintaining sterility of the liquid medication 12 without the necessity for added antibacterial preservative. Thus, the only necessary antibacterial material within the container is the liquid medication itself, assuming that the medication to be dispensed has antibacterial properties. Once sterile fluid or liquid medication or medicament is originally provided in the container, whether in solution, emulsion, or suspension form, there is no necessity of added antibacterial preservative in the liquid to be dispensed, for example, in liquid artificial tears. The design and structure of the novel device of the present invention morever fall within the range of economic reality for the mass production of a patient-dispensing disposable container to meet the commercial demands for such a novel and highly advantageous product.

In conclusion, from the foregoing, it is apparent that the present invention provides a novel disposable fluid medicament dispenser with a built-in filter, suitable for containment of a sterile fluid medicament, e.g., liquid artificial tears, therein, which permits elimination of antimicrobial or other preservative from the sterile fluid medicament contained therein, which is suitable for use in patient-administered medication, as well as a novel method of making and using the same, all having the foregoing enumerated characteristics and advantages.

It is to be understood that the invention is not to be limited to the exact details of operation, or to the exact compositions, methods, procedures, or embodiments shown and described, as obvious modifications and equivalents will be apparent to one skilled in the art, and the invention is therefore to be limited only by the full scope which can be legally accorded to the appended claims.

We claim:

1. An improved patient-dispensing container and medicament combination for releasing controlled amounts of a sterile liquid medicament while maintaining a sterile environment within the container, comprising:

a container housing member storing liquid medicament therein, the interior of which is in communication with a dispenser nozzle member having an outlet port, which nozzle member is secured to the housing member with a sterile liquid-tight connection, and filter means mounted within the dispenser nozzle member at the very outlet port thereof, said filter means including a series of hydrophilic hollow tubular filters providing egress openings or pores of not greater than approximately 0.2 micron in diameter, wherein the hollow tubular filters are secured with potting material in said nozzle and bent with their respective end openings aligned in the same direction, and means for transmitting the liquid medicament into the interior of the hollow tubular filters to cause egress thereof through the said egress openings or pores and out of said outlet port, whereby the sterile liquid medicament can be dispensed from said container while retaining sterility of the sterile liquid medicament remaining therein, thereby enabling the storage of a sterile liquid medicament in said container and dispensation of sterile liquid medicament from said container without the necessity of providing antibacterial or other preservative in said liquid medicament.

2. The combination of claim 1 wherein the tubular filters comprise a material which is a combination of cellulose nitrate, cellulose acetate, and glycerine.

3. An improved patient-dispensing container for releasing controlled amounts of a sterile liquid medicament contained therein while maintaining a sterile environment within the container, comprising:

a flexible housing member having a closure member for storing the liquid medicament and comprising a dispenser nozzle member with an outlet port;

filter means mounted within the dispenser nozzle member between the stored liquid medicament and the outlet port, and means for rigidly securing the filter means within the dispenser nozzle member to provide a sterile liquid-tight connection therebetween, the filter means including a series of hollow tubular filter members providing egress openings or pores of not more than approximately 0.2 micron in diameter, whereby sterile liquid medicament can be dispensed through the egress openings or pores while retaining the sterility of the contents of the container to enable the use of liquid medicament without the necessity of the presence of an antibacterial preservative therein, wherein the hollow tubular filter members are bent with their respective end openings positioned in the same direction and the means for rigidly securing the filter means in the nozzle member includes a potting material, and further including releasably securable closure cap means including means for periodically sterilizing the exterior surface of the outlet port of the dispenser nozzle member, wherein the sterilizing means includes a sterilizing material which contacts the exterior surfaced of the nozzle member at the outlet port thereof when said cap is secured to the nozzle member.

4. The dispensing container of claim 3 further including sterile filter means located in a vent in the container to assist transmission of sterile air into the housing member.

5. A combination of liquid medication, free of preservative agent, and a disposable sterile dispensing container which retains a sterile environment for the liquid medication during storage and dispensing, comprising:

a liquid-tight housing member for storing the liquid medication, a dispenser nozzle member having an outlet port connected to said housing member with a sterile liquid-tight connection, wherein the dispenser nozzle member nd the filter means are provided as an integral unit with the filter means rigidly sealed in the outlet port at the extreme outer end thereof, thereby to require the liquid medicament to pass only through the filter means during dispensing of the liquid medicament, a predetermined quantity of sterile liquid medication comprising a medicament and carrier fluid without added preservative agent in said housing member, said filter means having egress openings or pores of a size not greater than about 0.2 micron in diameter to prevent passage of bacteria therethrough, which filter means comprises bent hollow tubular filter members, the respective openings of the ends of the tubular filter members being positioned in the same direction and adjacent each other, and the means for rigidly securing the filter means in the nozzle member including a potting material.

6. A combination of claim 5, wherein the contained medicament and carrier fluid is liquid artificial tears.

7. The combination of claim 6 further including a sterile filter means mounted in a vent in said container to assist transmission of sterile air into the housing member.

8. The combination of claim 6 wherein the filter means comprises a material which is a combination of cellulose nitrate, cellulose acetate, and glycerine.

9. The combination of claim 6 further including releasably securable means for periodically sterilizing the exterior surface of the outlet port of the dispenser nozzle member.

10. The combination of claim 9 further including releasably securable closure cap means having means for retaining an antibacterial agent in contact with the exterior of the dispenser nozzle member when in place thereon.

11. The combination of claim 9 wherein the means includes releasably securable closure cap means comprising a sterilizing material which contacts the exterior surface of the nozzle member at the outlet port thereof when secured to the nozzle member.

* * * * *

UNITED STATES PATENT AND TRADEMARK OFFICE
CERTIFICATE OF CORRECTION

PATENT NO. : 5,105,993
DATED : Apr. 21, 1992
INVENTOR(S) : Peter G. La Haye, Peter W. Chan It is certified that error appears in the above-identified patent and that said Letters Patent is hereby corrected as shown below:

Column 2, line 33/34; after line 33 ending "art.", insert the
  heading -- SUMMARY OF THE INVENTION --.

Column 7, line 47/48; "or in filter-containment" should read
  -- or in a filter containment --.

Column 11, line 3;   "surfaced"     should read --surface --.

Column 11, line 19; "nd" should read -- and --.

Signed and Sealed this

Tenth Day of August, 1993

Attest:

MICHAEL K. KIRK

Attesting Officer        Acting Commissioner of Patents and Trademarks